United States Patent [19]

Falk et al.

[11] Patent Number: 4,512,343
[45] Date of Patent: Apr. 23, 1985

[54] MEDICAL COAGULATION DEVICE

[75] Inventors: Ernst Falk, Sternenfels-Diefenbach; Johann Knösel, Bretten, both of Fed. Rep. of Germany

[73] Assignee: Richard Wolf GmbH, Fed. Rep. of Germany

[21] Appl. No.: 488,379

[22] Filed: Apr. 25, 1983

[30] Foreign Application Priority Data

May 7, 1982 [DE] Fed. Rep. of Germany ....... 3217156

[51] Int. Cl.$^3$ ............................................. A61B 17/39
[52] U.S. Cl. ................................ 128/303.17; 174/111
[58] Field of Search ...................... 128/303.13–303.19, 128/783, 784–786, 788; 174/111

[56] References Cited

U.S. PATENT DOCUMENTS

| | | | |
|---|---|---|---|
| 426,201 | 4/1890 | Munsie | 174/111 |
| 1,844,501 | 2/1932 | Davis | 174/111 |
| 2,648,719 | 8/1953 | Smith et al. | 174/111 |
| 4,060,086 | 11/1977 | Storz | 128/303.15 |
| 4,128,099 | 12/1978 | Bauer | 128/303.17 |

FOREIGN PATENT DOCUMENTS

| | | | |
|---|---|---|---|
| 236968 | 4/1960 | Australia | 174/111 |
| 338369 | 6/1921 | Fed. Rep. of Germany | 174/111 |

*Primary Examiner*—Lee S. Cohen
*Attorney, Agent, or Firm*—Hill, Van Santen, Steadman & Simpson

[57] ABSTRACT

An insulated electrically conducted shaft for medical coagulation instruments, and particularly for unipolar coagulation instruments is constructed with an insulating jacket consisting of separate conduit pieces formed of insulating material which are slipped onto the shaft. The conduit pieces have abutting end faces which engage adjacent pieces in an overlapping fashion with the overlapping being caused by engagement of two layers of staggered conduit pieces of equal length or by complementary step formed end faces of adjacent conduit pieces or by inner diameter or outer diameter radial dimensioned steppings of the abutting conduit pieces with the resultant gaps filled by filler conduit pieces.

6 Claims, 5 Drawing Figures

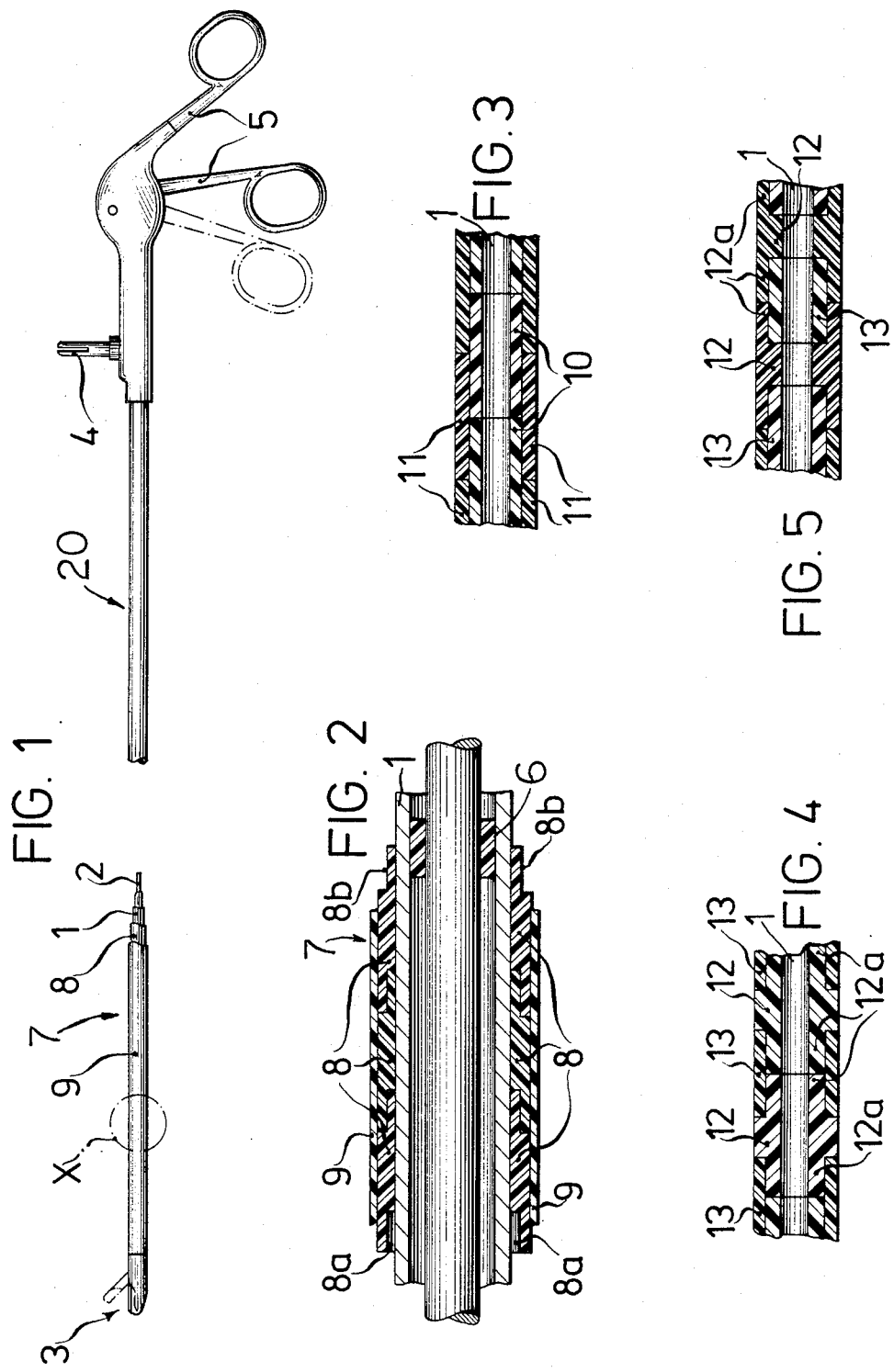

MEDICAL COAGULATION DEVICE

BACKGROUND OF THE INVENTION

1. Field of the Invention

This invention relates to medical instruments and more particularly to coagulation instruments of the type employing conductive shafts equipped with insulating jackets.

2. Prior Art

Medical coagulation instruments which employ conductive shafts are known. It is also known to provide the conductive shafts with an insulated jacket or shell and to terminate the shaft in an insulated handle provided for manipulation of the coagulation instrument.

Known coagulation instruments include unipolar coagulation devices such as forceps, etc., where the conductive shaft is generally surrounded by an insulating jacket applied over the length of the shaft with an additional insulating plastic hose or the like shrunk onto the jacket to preclude current leakage from the shaft to the body of the patient. Unfortunately, it has been shown that such known insulation means do not entirely satisfy safety expectations regarding prohibition of current leakage and, further, are relatively high in cost. It would therefore be an advance in the art to provide, particularly in unipolar coagulation instruments, an improved current leakage insulation for the instrument shaft which is both inexpensive and extremely safe.

SUMMARY OF THE INVENTION

It is therefore a principal object of this invention to provide an improved medical coagulation instrument having an electrically conductive shaft provided with a insulation jacket which is relatively low in cost and which is extremely safe in its prevention of current creepage or current leakage from the insulated shaft to the exterior of the insulated jacket.

This primary objective is achieved in that the insulating jacket is formed of a series of individual conduit pieces formed of insulation material which may be individually slipped over the shaft and which become joined together engaging one another in an overlapping fashion.

It is therefore possible to successively slip individual conduit pieces over the shaft in such a fashion that they will engage each other in an overlapping fashion along the length of the shaft. By selecting and choosing the overlap length with regard to the known creepage distance of the electric potentials employed, it can be assured that current leakage from the shaft to the patient will be prohibited. In this manner, although the use of a plurality of individual conduit lengths otherwise increases the gaps along the length of the shaft through which current could leak, each gap will be associated with a creepage path length which is great enough to safely prevent leakage.

The overlap engagement of the individual conduit pieces can be provided in a variety of ways. Additionally, the conduit pieces themselves can be manufactured in a simple manner, for example, from insulating plastic by means of injection molding. By using such techniques, it is possible to precisely meet desired wall thickness and overlap length requirements.

The individual conduit pieces equipped with the required wall thickness can, after being slipped over the shaft from an end thereof, be secured in position by cementing, thermobonding and other conventional plastic techniques. Finally, the instrument is preferably completed by application of a single piece overjacket which may, preferably, be of the shrink on plastic hose type.

In order to provide the desired overlap, the individual plastic conduit pieces may be formed with lapped ends with one axial end having a reduced thickness outer diameter axially projecting hose section and the opposed axial end having an increased inner diameter bore section with the sections having equal axial lengths. In this manner, the first axial end of one member will slip into the second axial end of the other member in a telescope manner with the axial end boss of one member inserted into the axial end counterbore of the other member. Alternatively, if desired, each of the primary shaft contacting conduit pieces could be formed with ledged, stepped or reduced outer diameter axial end sections at both axial ends and a secondary band conduit piece having an inner diameter equal to the reduced outer diameter of the shaft contacting pieces can be used to span the reduced outer diameter sections of adjacent and abutting shaft contacting pieces. The converse of this can also be provided where the individual primary conduit pieces consist of axial end counterbored members having a counterbore at each axial end. In that case, a secondary conduit piece an also be received over the shaft which has an axial length twice the counterbore length and therefore insertable into the counterbores of the adjacent conduit pieces. Finally, in its simplest expression, the conduit pieces may simply telescope one another in axial end overlapped position so that the inner conduit pieces are 50% lapped by outer conduit pieces.

Other objects, features and advantages of the invention will be readily apparent from the following description of a preferred embodiment thereof, taken in conjunction with the accompanying drawings, although variations and modifications may be effected without departing from the spirit and scope of the novel concepts of the disclosure, and in which:

BRIEF DESCRIPTION OF THE DRAWINGS

FIG. 1 is a side elevational view of a medical coagulation instrument with a portion thereof broken away showing telescoped portions of the instrument.

FIG. 2 is an enlarged fragmentary sectional view of a portion of the length of the instrument of FIG. 1, for example, taken at the area indicated at X on FIG. 1.

FIG. 3 is an enlarged fragmentary sectional view of a portion of the length of the instrument of FIG. 1 illustrating another embodiment of this invention.

FIGS. 4 and 5 are views similar to FIG. 3 illustrating additional embodiments of this invention.

DESCRIPTION OF THE PREFERRED EMBODIMENTS

FIG. 1 illustrates, in general, a standard type of medical coagulation forceps 20. Such forceps are generally of the unipolar type and consist of a metallic guide shaft 1 which guides a continuous axially mobile metallic working shaft or draw rod 2 which can be activated by the forceps handles 5. The shaft 1 is provided at its proximal end with a HF connection 4. By means of the working shaft 2, the tongs or rod mouth 3 can be actuated. The handle pieces 5 are electrically insulated to protect the operating personnel. The working shaft 2 may be centrally guided in the shaft 1 by means of a plurality of spacing elements 6. An exterior insulating jacket is provided to protect against current leakages from the shaft 1 to the body of the patient. The insulating jacket 7 may, according to this invention, consist of a plurality of individual plastic conduit pieces which may, for example, be manufactured by injection molding. Each of the individual pieces 8 are dimensioned to slip over the shaft 1 and are provided with abutting end faces which engage each other in an overlap.

A first preferred embodiment is illustrated in FIG. 2 where the insulating jacket 7 is constructed of similar conduit faces 8 which are of equal length and which are reduced in radial wall thickness at one end by an interior step or counterbore 8a and at the other end by an exterior step or radially reduced axial boss 8b. The end face steps are equal dimensioned such that a boss 8b may project into and fully seat in a counterbore 8a. In order to securely position the conduit pieces 8 on the shaft 1, individual, several or, if desired, all of the conduit pieces can be cemented or otherwise attached to the shaft and/or to each other.

Penetration of foreign matter into the joints between the individual conduit pieces and the related danger of current leakage due to current creepage can be effectively avoided by use of a plastic hose 9 as an additional or outer insulation jacket. The hose 9 can be shrunk onto the conduit pieces in a known manner, such as, for example, by use of heat shrink plastics. It will be appreciated that by use of the individual conduit pieces with the engaged overlap ends, each creepage gap is provided with two right angle turns and with a creepage length determined both by the radial thickness of the conduit pieces and by the axial length of the overlap. By proper choice of the overlap length in comparison to the radial thickness, it can be assured that electrical leakage will not occur. Moreover, by use of individual conduit pieces, the advantages of the insulated jacket according to this design can be economically provided for shafts of differing lengths merely by adding or subtracting to the total number of conduit pieces applied to the shaft. Moreover, should damage occur to a portion of the length of the instrument, the jacket portion can easily be replaced or, if desired, the entire jacket stripped and replaced.

FIG. 3 illustrates another, and in some respects, simpler embodiment of an insulated jacket according to this invention. In FIG. 3, the individual conduit pieces of the insulated jacket are provided with a uniform wall thickness from the inner to the outer diameters. In this embodiment, however, two different diameter conduit pieces 10 and 11 are provided with a first conduit piece having an inner diameter designed to be slipped over the shaft 1 and a second conduit piece 11 having an inner diameter designed to be slipped over the first conduit piece 10. By staggering the conduit pieces so that the axial ends of the outer layer of conduit pieces 11 rest at approximately the mid points of the axial lengths of the inner conduit pieces 10, a gap creepage path equivalent to that shown in FIG. 2 can be provided. Again, if desired, the outer shrink hose 9 can be utilized to prevent entry of contaminants into the gap areas and the individual conduit pieces can be bonded to the shaft or to one another if desired.

FIG. 4 illustrates a further embodiment of this invention where a plurality of axially abutting shaft encircling conduit pieces 12 are provided which have external steps at each axial end thereof providing axial projecting boss ends 12a at each of the axial ends of the conduit piece 12. Secondary conduit pieces 13 provided with an inner diameter equal to the outer diameter of the projecting bosses 12a and having a length twice the length of an individual projecting boss 12a are then used to span the axial distance between the unstepped outer diameter portions of adjacent conduit pieces 12. It will be understood of course that the conduit pieces 13 have an inner diameter equal to the outer diameter of the projecting bosses and a thickness approximately equal to the radial depth of the step providing the bosses.

FIG. 5 illustrates an embodiment similar but opposite to that of FIG. 4. In this embodiment, each of the conduit pieces 12 are provided with inner diameter steps or axial end counterbores 12a with the counterbores of each conduit piece lying in opposition to a counterbore of the adjacent conduit piece 12. The conduit counterbores are then filled with a secondary conduit piece 13 having an outer diameter equal to the inner diameter of the counterbore and an axial length twice the axial depth of the counterbore. It will be appreciated that in the embodiments of FIG. 4 and FIG. 5 the resultant gaps are again provided with the double right angle turn and the creepage length equivalents of FIG. 2. It will further be appreciated that in the case of the embodiments of FIGS. 4 and 5, a plastic hose 9 may be shrunken onto the outer diameter of the insulating jacket 12, 13 after the conduit pieces are fixed on the shaft 1.

Although the teachings of my invention have herein been discussed with reference to specific theories and embodiments, it is to be understood that these are by way of illustration only and that others may wish to utilize my invention in different designs or applications.

We claim as our invention:

1. A medical coagulation instrument comprising an electrically conductive hollow shaft member having proximal and distal ends and having an insulated handle affixed thereto at its proximal end and a manipulatable device operatively affixed thereto at its distal end and means for applying an electrical potential to said shaft member, an insulating jacket surrounding said shaft member for at least a portion of its length between the proximal and distal ends thereof, said insulating jacket comprising a plurality of individual axially abutting conduit pieces surrounding said shaft member, said conduit pieces formed of insulating material, said conduit pieces being dimensioned to be slipped over said shaft member and said conduit pieces having axial end faces abutting axial end faces of adjacent conduit pieces, the end faces of said conduit pieces abutting in such a manner as to provide a contact line of end face abutment between the inner diameter and the outer diameter of the jacket which has two radial components separated by an axial component.

2. An instrument according to claim 1, wherein the insulating jacket consists of radially inner and radially outer layers of telescoped individual plastic conduit pieces, each of said layers containing a plurality of such conduit pieces, the outer layer having axial ends of the conduit pieces positioned axially intermediate the axial ends of the conduit pieces of the inner layer, each of said conduit pieces being substantially of equal length and wall thickness.

3. An instrument according to claim 1, wherein the insulating jacket consists of a plurality of conduit pieces having first and second axial ends, a first axial end having a counterbore therein, a second axial end having an outer diameter step forming an axial projecting boss of smaller outer diameter, the boss of one conduit piece being inserted into and substantially filling the counterbore of an axially adjacent conduit piece.

4. An instrument according to claim 1, wherein the insulating jacket consists of a plurality of primary conduit pieces having reduced outer diameters adjacent the axial ends thereof providing stepped axial ends, said primary pieces being arranged along said shaft in abutting relation, a plurality of secondary conduit pieces having inner diameters equal to the outer diameters of the stepped axial end portions of said primary conduit pieces and being received around said primary conduit pieces overlying said stepped axial ends, the secondary conduit pieces having a length dimensioned to substantially encompass the stepped ends of adjacent primary conduit pieces, the secondary conduit pieces having an outer diameter substantially equal to the unstepped portion outer diameter of the primary conduit pieces.

5. A coagulation instrument according to claim 1, wherein said jacket consists of a plurality of primary conduit pieces having first and second axial ends having counterbores formed therein positioned along said shaft member in abutting relationship and a plurality of secondary conduit pieces received in said counterbores having an inner diameter substantially equal to the outer diameter of the shaft member and an outer diameter substantially equal to the inner diameter of the counterbores and a length substantially equal to the length of the primary conduit pieces abutting counterbores whereby the counterbores are substantially filled by said secondary conduit pieces.

6. A medical coagulation instrument having distal and proximal ends and having an electrically conductive hollow shaft with an electrically insulated handle affixed thereto at said proximal end thereof and a manipulative member operatively connected thereto at said distal end thereof, with means for applying an electrical potential to said shaft, an insulation jacket surrounding said shaft intermediate the proximal and distal ends, said insulation jacket consisting of a plurality of individual conduit pieces dimensioned to be slipped over said shaft and axially abutting one another along the length of said shaft, each of said conduit pieces having first and second axial end faces, said axial end faces abutting adjacent axial end faces of adjacent conduit pieces in an overlapping abutment, and a single insulative shrink fit member received around said conduit pieces substantially along the length of said jacket.

* * * * *